| United States Patent [19] | | [11] | Patent Number: | 4,852,582 |
|---|---|---|---|---|
| Pell | | [45] | Date of Patent: | Aug. 1, 1989 |

[54] METHOD AND KIT FOR MEASURING THE EFFECTIVENESS OF BRONCHODILATORS

[76] Inventor: Donald M. Pell, P. O. Box 31647, St. Petersburg, Fla. 33732

[21] Appl. No.: 95,232

[22] Filed: Sep. 11, 1987

[51] Int. Cl.$^4$ ................................................. A61B 5/08
[52] U.S. Cl. ..................................... 128/716; 128/725
[58] Field of Search ............... 128/716, 725, 726, 727, 128/728, 729

[56] References Cited

U.S. PATENT DOCUMENTS

| 3,721,228 | 3/1973 | Prediger et al. | 128/716 |
|---|---|---|---|
| 3,949,737 | 4/1976 | Nielsen | 128/726 |
| 4,158,360 | 6/1979 | Adams | 128/725 |
| 4,210,155 | 7/1980 | Grimes | 128/727 |
| 4,558,710 | 12/1985 | Eichler | 128/725 |
| 4,736,750 | 4/1988 | Valdespino et al. | 128/725 |

FOREIGN PATENT DOCUMENTS

| 1281247 | 1/1987 | U.S.S.R. | 128/725 |
|---|---|---|---|

Primary Examiner—Lee S. Cohen
Assistant Examiner—John C. Hanley
Attorney, Agent, or Firm—Bacon & Thomas

[57] ABSTRACT

A method and kit for measuring the effectiveness of various bronchodilators on an individual patient are disclosed. For example, the kit includes a plurality of bronchodilator test solutions and a nebulizer for providing a dose of each solution for introduction into a patient's lungs. A spirometer or other type of flowmeter is also provided for measuring the flow characteristics of a patient's forced expiratory flow before and after inspiration of each of the bronchodilator solutions. A test panel is also provided for recording and comparing the patient's flow data before and after inspiration of each of the test solutions. And, in a preferred embodiment of the invention, the patient's lungs are rechallenged to verify the best treatment for the patient. And, a second embodiment includes instructions and a peak flow meter in place of a spirometer, so that the tests may be self-administered in a patient's home.

10 Claims, 2 Drawing Sheets

| DRUG OF CHOICE | PRE FEV$_1$ | POST FEV$_1$ | PRE VITAL CAP. | POST VITAL CAP. | BEST 2 SOLUT. | FINAL FEV$_1$ |
|---|---|---|---|---|---|---|
| ALUPENT 0.3 ml. | | | | | | |
| BRONKOSOL 0.5 ml. | | | | | | |
| TERBUTALINE 1 mg. | | | | | | |
| VENTALIN 0.5 ml. | | | | | | |
| ALUPENT 0.3ml + ATROPINE SULFATE 0.8g | | | | | | |
| BRONKOSOL 0.5ml. + ATROPINE SULFATE 0.8g | | | | | | |
| TERBUTALINE 1mg. + ATROPINE SULFATE 0.8g | | | | | | |
| VENTALIN 0.5mg + ATROPINE SULFATE 0.8g | | | | | | |

| DRUG OF CHOICE | PRE FEV$_1$ | POST FEV$_1$ | PRE VITAL CAP. | POST VITAL CAP. | BEST 2 SOLUT. | FINAL FEV$_1$ |
|---|---|---|---|---|---|---|
| ALUPENT 0.3 ml. | | | | | | |
| BRONKOSOL 0.5 ml. | | | | | | |
| TERBUTALINE 1 mg. | | | | | | |
| VENTALIN 0.5 ml. | | | | | | |
| ALUPENT 0.3ml + ATROPINE SULFATE 0.8g | | | | | | |
| BRONKOSOL 0.5ml. + ATROPINE SULFATE 0.8g | | | | | | |
| TERBUTALINE 1mg. + ATROPINE SULFATE 0.8g | | | | | | |
| VENTALIN 0.5mg + ATROPINE SULFATE 0.8g | | | | | | |

FIG 1

| DRUG OF CHOICE | PRE FEV$_1$ | POST FEV$_1$ | PRE VITAL CAP | POST VITAL CAP | BEST 2 SOLUT. | FINAL FEV$_1$ |
|---|---|---|---|---|---|---|
| ALUPENT 0.3 ml. | 480 | 520 | 1730 | 1780 | | |
| BRONKOSOL 0.5 ml. | 880 | 1490 | 1630 | 2150 | | |
| TERBUTALINE 1 mg. | 1000 | 2550 | 1740 | 2550 | ✓ | |
| VENTALIN 0.5 ml. | | | | | | |
| ALUPENT 0.3ml. + ATROPINE SULFATE 0.8g | 980 | 1480 | 1580 | 2220 | | |
| BRONKOSOL 0.5ml. + ATROPINE SULFATE 0.8g | 1320 | 1360 | 1220 | 2270 | | |
| TERBUTALINE 1mg. + ATROPINE SULFATE 0.8g | 480 | 2330 | 1290 | 2480 | ✓ | |
| VENTALIN 0.5mg + ATROPINE SULFATE 0.8g | | | | | | |

FIG 2

FIG 5
PEAK EXPIRATORY FLOW
| | TEST 1 | | 2 | | 3 | | 4 | | 5 | | 6 | |
|---|---|---|---|---|---|---|---|---|---|---|---|---|
| | PRE PEV | POST PEV | PRE | POST | PRE | POST | PRE | POST | PRE | POST | PRE | POST |
| ALUPENT + ATROPINE SULFATE 0.8g | | | | | | | | | | | | |
| BRONKOSOL + ATROPINE SULFATE 0.8g | | | | | | | | | | | | |
| BREATHINE + ATROPINE SULFATE 0.8g | | | | | | | | | | | | |
| VENTALON + ATROPINE SULFATE 0.8g | | | | | | | | | | | | |
FIG 3
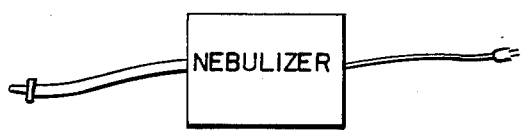
FIG 4
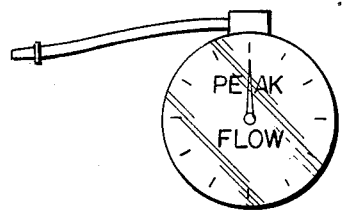
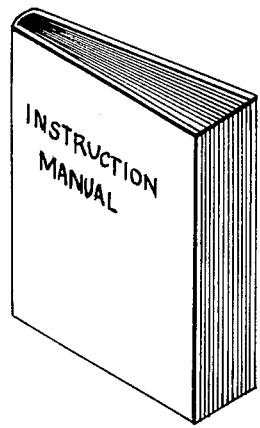
FIG 6

METHOD AND KIT FOR MEASURING THE EFFECTIVENESS OF BRONCHODILATORS

BACKGROUND OF INVENTION

This invention relates to a method and kit for measuring the effectiveness of bronchodilators on an individual patient. The invention relates more particularly to a method and kit for providing a quantitative comparison, so that a physician can select the most effective treatment for a patient.

Physicians have for many years used spirometers to test for reversible airway diseases such as asthma. In fact, spirometry is considered to be the single most useful test for evaluating asthma. Physicians have also used spirometers for bronchodilator studies. And, in conducting such studies, the physician or technician has a patient exhale before and after inhaling a bronchodilator from a metered-dose aerosol generator. And, the patient is instructed to hold the inspired volume of aerosol for at least several seconds before exhalation.

In conducting spirometer tests, the spirometer indicates the volume, flow, and ventilation capacities of the respiratory system. For example, the spirometer is commonly used to measure the following:

Vital Capacity (VC); the maximum volume of air exhaled from the point of maximum inspiration;

Forced Vital Capacity (FCV); is the vital capacity performed with a maximally forced expiratory effort;

Timed Forced Expiratory Volume ($FEV_T$); is the volume of air exhaled in the specified time during the performance of the forced vital capacity;

Forced Expiratory Volume I ($FEV_I$); is the volume of air exhaled during the first second of the FVC; and Peak Expiratory Flow (PEF); is the maximum rate of flow exhaled during a forced expiration of the lungs.

In the past it has been generally assumed that known bronchodilators are statistically equivalent. Accordingly, many physicians consider that an individual patient's lungs react differently to treatment with different bronchodilators. Other physicians have resorted to trial and error methods for determining which bronchodilator is best for which patient. Prior studies also assumed that bronchodilators should be withheld from the patient for a period of at least 6 or 8–12 hours prior to the test. See, for example, Pulmonary Diseases-Focus on Clinical Diagnosis, pp. 50 and 222, Medical Examination Publishing Co., Inc. 1983.

It has now been found that individual patients react differently to treatment with different bronchodilators. It has also been found that a series of tests can be conducted in a relatively short period of time to obtain and verify quantitative date which will enable a physician to prescribe a preferred treatment for a particular patient.

SUMMARY OF THE INVENTION

In essence a kit according to the present invention include a plurality of bronchodilator test solutions and a nebulizer for providing a dose of each test solution for introduction into a patient's lungs for example by inspiration by the patient. A measuring device such as a portable spirometer or flowmeter such as a Wright's Peak flowmeter is provided for measuring the patient's forced expiratory flow data. A test panel is also included for recording the flow data before and after inspiration of each bronchodilator and for visual comparison of the quantitative results of the tests to thereby indicate a preferred treatment.

A kit, in accordance with a preferred embodiment of the invention, includes 8 bronchodilator test solutions and a measured dose nebulizer for providing a premeasured amount of each test solution for inspiration by a patient. An electronic spirometer such as a Respiradyne Pulmonary Function Monitor, Model 5-7905 is also provided for measuring a patient's vital capacity and forced expiratory volume in the first second of a forced vital capacity test before and after inspiration of each of the test solutions. A test panel is included for recording and comparing the vital capacities and forced expiratory volume in the first second of expiration before and after the inhalation of each nebulized test solution. The test panel also includes space for verification of the two best tests in the first series.

The invention also contemplates a method for challenging a patient's lungs to determine which in a series of bronchodilator test solutions is most effective for treating an individual patient. The method includes the steps of providing a plurality of bronchodilator test solutions, nebulizing the solutions and introducing the nebulized solution into a patient's lungs.

The method also includes the steps of measuring and recording the flow characteristics of a patient before and after introducing each nebulized bronchodilator solution into the patient's lungs. A comparison of the flow data such as vital capacity or $FEV_I$ enables a physician to select the best treatment for a particular patient.

The invention will now be described in connection with the accompanying drawings.

BRIEF DESCRIPTION OF THE DRAWINGS

FIG. 1 illustrates a test panel for use with a bronchodilator test kit according to a preferred embodiment of the invention; and, FIG. 2 illustrates a test panel as shown in FIG. 1 but which includes the comparative data for an individual patient.

FIG. 3 is a schematic illustration of, for example, a nebulizer, a DeVilbis Air Compressor Series 561 for nebulizing the bronchodilators prior to inspiration by a patient;

FIG. 4 is a schematic illustration of a flow meter or spirometer for example a Respiradyne Pulmonary Function Monitor Model 5-7905 for measuring the vital capacity, $FEV_I$ or peak expiratory flow (PEF) before and or after inspiration of a bronchodilator;

FIG. 5 illustrates a test panel for use in home testing of the peak expiratory flow before and after inspiration of a bronchodilator; and, FIG. 6 is a schematic illustration of an instruction manual for conducting bronchodilator tests and recording flow data.

DETAILED DESCRIPTION OF THE INVENTION

In essence, a bronchodilator test kit, according to a preferred embodiment of the invention, is designed for use in a hospital. And, the use of the kit provides a physician and patient with a quantitative measure of the effectiveness of various bronchodilators on an individual patient.

The test kit includes a plurality of bronchodilator test solutions as shown in FIGS. 1 and 2. For example, each kit includes the following test solutions: Alupent, Bronkosol, Brethine, Ventolin, Alupent and Atropine, Bronkosol and Atropine, Brethine and Atropine, and Ventolin and Atropine. These bronchodilators are referred to by their trade names which are readily recognized by physicians. However, the generic names for the bronchodilators are as follows. Alupent is a tradename for metaproterenol, Bronkosol for isoetherine, Brethine for terbutaline, Ventolin for albuterol and Atropine is Atropine Sulfate 0.8 mg.

The test solutions are typically saline containing 5% of the bronchodilator dispersed therein. Typical dosages are 0.3 ml of a 5% solution of Alupent, 0.5 ml of a 0.125% solution of Bronkosol, 1 ml of a 1% solution of Brethine and 0.5 ml. of a 5% solution of Ventolin. In addition, the dosages of the above are mixed with 0.8 mg. of atropine which may be in a 5% saline solution for testing each bronchodilator with an anticholinergic.

The test kit according to the preferred embodiment of the inventions also includes a nebulizer as illustrated in FIG. 3. The nebulizer is preferrably a measured dose nebulizer such as a DeVilbis Compression Series 561. However, any type of nebulizer may be used, provided that it will provide an adequate volume of bronchodilator for inhalation by a patient and for dispersion in the lungs.

A spirometer as illustrated in FIG. 4 is also included for measuring the vital capacity of a patient's lungs before and after inspiration of the bronchodilators. A portable electronic spirometer such as a Respiradyne Pulmonary Function Monitor Model 5-7905 is preferred, however, an office or laboratory spirometer such as a Breon model 2400, manufactured by Breon Laboratories Inc., New York, N.Y., may be used.

A test panel as illustrated in FIGS. 1 and 2 includes a list of bronchodilator test solutions which are included in the kit. The test solutions are preferrably displayed along a vertical axis. And a plurality of vertical columns divided by horizontal lines follows the list of solutions and define a rectangular matrix for listing the flow characteristics of a patient's expiration before and after inspiration of each solution.

The columns include headings at the top thereof to indicate vital capacity (VC) and forced expiratory volume in the first second of expiration ($FEV_1$) in cubic centimeters before and after inspiration of a nebulized bronchodilator test solution. The panel or matrix also includes columns and names for recording the results of a second series of tests. However in practice, the second series of tests is limited to the two solutions which produced the maximum improvement in breathing during the first sequence of tests.

The second sequence of tests, i.e., the two preferred test solutions are conducted to verify the results of the first test. And in many cases, the second test verifies that the preferred bronchodilator from the first test is in fact the preferred solution. Nevertheless, there are a significant number of patients in which the preferred solution from the first proves to be less effective during the second test. The more effective bronchodilator from the second test is then the preferred medication. For this reason, it is recommended that a physician rechallenge the lung to verify the best treatment for an individual patient.

In addition, a typical set of instructions provide the following information for the technician administering the tests:

EQUIPMENT (1) IPPB or Handheld Nebulizer.
(2) Bronchodilator drugs to be used.
(3) Breon Pulmonary Function Machine.
(4) Bronchodilator Panel For Evaluation.

PROCEDURE (1) Check chart for Panel Order.
(2) Explain to the patient what his doctor wants to find out;
(3) Set up Pulmonary Function equipment and do three (3) $FEV_1$'s and VCs prior to first treatment.
(4) Record on the panel notes the $FEV_1$, VC and the first drug to be used.
(5) If the $FEV_1$ is less than 1.0 liter use IPPB to deliver medication. If $FEV_1$ is more than 1.0 liter use a hand held Nebulizer.
(6) Administer first drug on panel.
(7) After therapy is completed report $FEV_1$ and VC measured with Breon spirometer, Respiradyne Pulmonary Function Monitor Model 5-7905 and record in spaces for post $FEV_1$ and VC.
(8) Record normal and/or abnormal parameters monitored or observed during therapy. For example, respiratory rate, pulse, breath sounds and any adverse reactions to the medication, e.g., pulse greater than 120, chest pain, worse shortening of breath, shakiness, should be noted and called to the physician's attention.
(9) Repeat this process with each drug allowing 4 hours between tests until all have been tried.
(10) When the entire panel is completed, place a copy in the Respiratory Therapy notes.
(11) Make out a treatment card and complete the record, keeping on the Bronchodilator Panel.
(12) After completing the panel study, compare the two drugs which gave the best response based on $FEV_1$ and retest using only those two drugs. Then, notify the physician of the results.

A bronchodilator test kit, according to a second embodiment of the invention, is designed for home use. Tests based on the use of this kit are self-administered and results are recorded by the patient. Therefore, the test includes a relatively detailed set of instructions as schematically shown in FIG. 6.

For example, the patient is advised to inspire and expire a maximum volume of air for each test. The patient is also advised that the inspired volume of bronchodilator should be held for several seconds before expiration and that post treatment measurements should be taken about eight to ten minutes after expiration of the bronchodilator.

An anticholinergic such as atropine has a synergistic effect on bronchodilators. Therefore, most bronchodilator treatments include a bronchodilator with atropine or some other anticholinergic. Bronchodilator treatments also typically provide for a treatment every four hours or six treatments a day.

It has now been found that a bronchodilator test kit for home testing should include four bronchodilator test solutions each of which include an anticholinergic such as atropine. It is also desirable to test a patient with a single bronchodilator test solution at least several times during the day and to record the expiratory flow data before and after each treatment. In the preferred format a patient will test the expiratory flow before and after each of the six treatments during a 24 hour period.

It should be recognized that the self-administered tests are less precise and will not necessarily provide as much meaningful data as the in-hospital tests. However, the self-administered tests are adequate in many cases for selecting the more effective treatment for a patient.

It should also be recognized that the bronchodilator test kits, according to this embodiment of the invention, include a Wright peak flowmeter in place of a spirometer. It is possible to include an electronic spirometer in place of the peak flowmeter for home use. However, the added costs over that of a Wright peak flowmeter is significant. Accordingly, the home evaluation of bronchodilators is generally based on a plurality of tests and on the before and after peak expiratory flow data. And while such data may be less accurate than that provided by the in-hospital testing, it is sufficient for many patients whose illnesses do not require hospitalization.

Therefore, the test panel for the at-home kit illustrated in FIG. 5 is significantly different than those shown in FIGS. 1 and 2. For example, the test panel includes a vertical listing of four bronchodilators and 12 vertical columns for recording the peak expiratory flow before and after each of the six tests which are to be done daily on an every four hour basis.

And, at the end of four days of testing, the patient returns to the doctor's office with the comparative data. It should be noted that improvements of 15 to 25% of the initial pretesting value are considered slight, 25% to 50% moderate, and greater than 50% is indicative of marked improvement. It should also be noted that the differences between the results with one bronchodilator and that of another are significant and readily apparent to both the physician and patient.

This quantitative evidence is effective not only for prescribing the most effective therapy but also in convincing a patient to adhere to the prescribed treatment. For example, some patients who are not convinced of the effectiveness of their treatment are less than diligent in adhering to scheduled treatments. However, with visual evidence of the effectiveness of therapy, they are more likely to follow their doctor's recommendations.

In essence, the methods of the present invention include the steps of providing a plurality of bronchodilator test solutions with and/or without an anticholinergic such as atropine; measuring a patient's expiratory flow data such as vital capacity, forced expiratory volume in the first second of expiration, or peak expiratory flow and recording such data. A first of the bronchodilator test solutions is nebulized, inspired by a patient or introduced into a patient's lungs by using a nebulizer, and held within the patient's lungs for several seconds. And, 8 to 10 minutes after inspiration of the bronchodilator, the patient's expiratory flow is measured and recorded.

Then, after waiting for at least 4 hours, the procedures are repeated using a second bronchodilator test solution. And after waiting an additional period of at least 4 hours, the procedures are repeated with a third bronchodilator test solution and so forth until the patient has been tested with each of the test solutions.

In the preferred method, the patient's vital capacity and $FEV_1$ are measured using a spirometer. And, comparing the data clearly indicate the preferred treatment for a particular patient. In general, the physician compares the $FEV_1$ for determining the best treatment for the patient. However, the vital capacity may also be used in determining respiratory problems which can effect treatment as will be readily understood by pulmonary physicians.

In conducting tests at home, the patient follows essentially the same procedure as above but conducts a series of six before and after tests with a single bronchodilator solution during a 24 hour period. And, then the second, third, and fourth solution are tested on subsequent days. And, in conducting the at-home test, the patient measures and records peak expiratory flow. The physician and patient then compare the data and agree on the best therapy.

While the invention has been described with respect to its preferred embodiments, it will be obvious that various modifications may be made by those skilled in the art without departing from the scope of the following claims.

What is claimed is:

1. A kit for measuring the effectiveness of various bronchodilators on an individual patient comprising a plurality of bronchodilator test solutions and a nebulizer means for providing a measured dose of each test solution for introduction into a patient's lungs, means for measuring a patient's forced expiratory flow data and a test panel means for recording the flow data before and after inspiration of each of the plurality of bronchodilator test solutions and for visual comparison of the quantitative results for determining the effectiveness of the bronchodilators.

2. A kit for measuring the effectiveness of bronchodilators in an individual patient according to claim 1 in which the bronchodilator test solutions include saline solutions of metaproterenol with atropine sulfate, isoetherine with atropine sulfate, terbutaline with atropine sulfate and albuterol with atropine sulfate, and in which the means for measuring the patient's forced expiratory flow data is a peak flowmeter and in which the test panel means includes designated spaces for recording peak expiratory flow and the kit includes a set of instructions for self administration of the test.

3. A kit for measuring the effectiveness of bronchodilators in an individual patient according to claim 2 in which there is a sufficient amount of each of said test solutions for conducting at least four tests and wherein the test panel means includes designated spaces for recording the results of the four tests.

4. A kit for measuring the effectiveness of bronchodilators in an individual patient according to claim 1 in which said plurality of bronchodilator test solutions include eight saline solutions of metaproterenol, isoetherine, terbutaline and albuterol with and without 0.8% mg of atropine sulfate and in which the means for measuring the patient's forced expiratory flow data is a spirometer and the test panel includes designated spaces for recording a patient's vital capacity and forced expiratory volume during the first second of expiration before and after each test of a bronchodilator solution.

5. A kit for measuring the effectiveness of bronchodilators in an individual patient according to claim 4 in which there is a sufficient amount of each of said test solutions for conducting two tests and wherein the test panel means includes designated spaces for recording the results of both tests.

6. A kit for measuring the effectiveness of bronchodilators in an individual patient according to claim 4 in which the measured does are as follows: 0.3 ml. of a 5% saline solution of metaproterenol, 0.5% ml of a 0.125% saline solution of isoetherine, 1.0 ml of a 1% saline solution of terbutaline, 0.5 ml of a 5% saline solution of albuterol and each of the aforementioned doses mixed with 0.8 ml of a saline solution of atropine sulfate.

7. A method for measuring the effectiveness of bronchodilators on an individual patient comprising the steps of:
   a. providing a plurality of bronchodilator test solutions;
   b. measuring and recording the forced expiratory flow of the patient after at least 4 hours following after any use of a bronchodilator;
   c. nebulizing a first one of the test solutions;
   d. introducing the nebulized solution into the patient's lungs and maintaining the nebulized solution therein for at least several seconds before expiration thereof;
   e. waiting for a period of at least about 8 minutes;
   f. measuring and recording the forced expiratory flow of the patient during the first second of forced expiration;
   g. waiting for a period of at least about four hours without additional inhalation of a bronchodilator; and
   h. repeating steps a through g for each of the remaining bronchodilators until step f has been completed for the last test solution; and
   i. comparing any improvement in post treatment flow over the pretreatment flow for each of the bronchodilator test solutions and determining the most effective treatment for the patient.

8. A method for measuring the effectiveness of bronchodilators in an individual patient according to claim 7 wherein at least one of the plurality of bronchodilators includes an anticholinergic, and wherein steps b-f include the steps of measuring and recording the vital capacity and forced expiratory volume in the first second of expiration.

9. A method for measuring the effectiveness of bronchodilators in an individual patient according to claim 8 wherein multiple tests are performed with each of the bronchodilator solutions and in which peak expiratory flow is measured and recorded before and after each of the tests.

10. A method for measuring the effectiveness of bronchodilators in an individual patient according to claim 7 which includes the step of displaying the forced expiratory flow during the first second of expiration and further including the step of rechallenging the lungs by retesting the two bronchodilator test solutions which provided the maximum improvements during the first series of tests to thereby verify which is the best treatment for the patient.

* * * * *